United States Patent
Cheng et al.

(10) Patent No.: US 10,145,669 B2
(45) Date of Patent: Dec. 4, 2018

(54) REDUCING SPECKLE NOISE IN OPTICAL COHERENCE TOMOGRAPHY IMAGES

(71) Applicants:AGENCY FOR SCIENCE, TECHNOLOGY AND RESEARCH, Singapore (SG); KABUSHIKI KAISHA TOPCON, Tokyo (JP)

(72) Inventors: Jun Cheng, Singapore (SG); Jiang Liu, Singapore (SG); Lixin Duan, Singapore (SG); Yanwu Xu, Singapore (SG); Wing Kee Damon Wong, Singapore (SG); Masahiro Akiba, Tokyo (JP)

(73) Assignees: AGENCY FOR SCIENCE, TECHNOLOGY AND RESEARCH, Singapore (SG); KABUSHIKI KAISHA TOPCON, Tokyo (JP)

( * ) Notice: Subject to any disclaimer, the term of this patent is extended or adjusted under 35 U.S.C. 154(b) by 0 days.

(21) Appl. No.: 15/319,360

(22) PCT Filed: Jun. 16, 2015

(86) PCT No.: PCT/SG2015/050162
§ 371 (c)(1),
(2) Date: Dec. 15, 2016

(87) PCT Pub. No.: WO2015/195048
PCT Pub. Date: Dec. 23, 2015

(65) Prior Publication Data
US 2017/0131082 A1    May 11, 2017

(30) Foreign Application Priority Data
Jun. 16, 2014 (SG) .......................... 10201403294R

(51) Int. Cl.
*G06T 5/20* (2006.01)
*G01B 9/02* (2006.01)
(Continued)

(52) U.S. Cl.
CPC .......... *G01B 9/02082* (2013.01); *A61B 3/102* (2013.01); *G01B 9/02091* (2013.01);
(Continued)

(58) Field of Classification Search
None
See application file for complete search history.

(56) References Cited

U.S. PATENT DOCUMENTS

2007/0196018 A1* 8/2007 Chen ...................... G06T 7/238
382/209
2008/0100612 A1 5/2008 Dastmalchi et al.
(Continued)

FOREIGN PATENT DOCUMENTS

| EP | 2 141 506 A2 | 1/2010 |
| JP | 2004-088462 A | 3/2004 |
| JP | 2010-057899 A | 3/2010 |

OTHER PUBLICATIONS

Wikipedia, "Optical coherence tomography", Dated Apr. 22, 2010.*
(Continued)

*Primary Examiner* — Matthew Bella
*Assistant Examiner* — Brian Shin
(74) *Attorney, Agent, or Firm* — Womble Bond Dickinson (US) LLP

(57) ABSTRACT

A method and system are proposed to obtain a reduced speckle noise image of a subject from optical coherence tomography (OCT) image data of the subject. The cross sectional images each comprise a plurality of scan lines obtained by measuring the time delay of light reflected, in a depth direction, from optical interfaces within the subject. The method comprises two aligning steps. First the cross sectional images are aligned, then image patches of the aligned cross sectional images are aligned to form a set of aligned patches. An image matrix is then formed from the
(Continued)

aligned patches; and matrix completion is applied to the image matrix to obtain a reduced speckle noise image of the subject.

16 Claims, 4 Drawing Sheets

(51) Int. Cl.
    *G06T 7/00*     (2017.01)
    *G06T 5/00*     (2006.01)
    *G06T 5/50*     (2006.01)
    *A61B 3/10*     (2006.01)
    *G06T 7/32*     (2017.01)
    *G06T 7/33*     (2017.01)

(52) U.S. Cl.
    CPC ............... *G06T 5/002* (2013.01); *G06T 5/20* (2013.01); *G06T 5/50* (2013.01); *G06T 7/0014* (2013.01); *G06T 7/32* (2017.01); *G06T 7/337* (2017.01); *G06T 2207/10016* (2013.01); *G06T 2207/10101* (2013.01); *G06T 2207/20021* (2013.01); *G06T 2207/20024* (2013.01); *G06T 2207/20221* (2013.01); *G06T 2207/30041* (2013.01)

(56) References Cited

U.S. PATENT DOCUMENTS

| | | | |
|---|---|---|---|
| 2008/0231502 A1* | 9/2008 | Allen | ............... G06T 5/002 342/25 F |
| 2010/0004527 A1 | 1/2010 | Dale et al. | |
| 2014/0126839 A1* | 5/2014 | Qin | ............... G06T 3/0068 382/294 |

OTHER PUBLICATIONS

PCT International Search Report for PCT Counterpart Application No. PCT/SG2015/050162, 3 pp., (dated Sep. 8, 2015).

PCT Written Opinion of the International Searching Authority for PCT Counterpart Application No. PCT/SG2015/050162, 4 pp., (dated Sep. 8, 2015).

B. Sander, et al., "Enhanced Optical Coherence Tomography Imaging by Multiple Scan Averaging", British Journal of Ophthalmology, vol. 89, No. 2, pp. 207-212, (2005).

Rick MA, et al., "Decomposition Approach for Low-Rank Matrix Completion and Its Applications", IEEE Transactions on Signal Processing, vol. 62, No. 7, pp. 1671-1683, (Apr. 1, 2014).

Yongjian Yu, et al., "Speckle Reducing Anisotropic Diffusion", IEEE Transactions on Image Processing, vol. 11, No. 11, pp. 1260-1270, (Nov. 2002).

Shan Zhu, et al., "A New Diamond Search Algorithm for Fast Block-Matching Motion Estimation", IEEE Transactions on Image Processing, vol. 9, No. 2, pp. 287-290, (Feb. 2000).

Jun Cheng, et al., "Speckle Reduction in Optical Coherence Tomography by Matrix Completion using Bilateral Random Projection", 2014 36th Annual International Conference of the IEEE Engineering in Medicine and Biology Society (EMBC), pp. 186-189, (Aug. 2014).

PCT Notification Concerning Transmittal of International Preliminary Report on Patentability (Chapter 1 of the Patent Cooperation Treaty) for PCT Counterpart Application No. PCT/SG2015/050162, 6 pp., (dated Dec. 29, 2016).

Supplementary European Search Report for counterpart European Patent Application No. 15809094, 2 pgs. (dated Oct. 19, 2017).

Maciej Szkulmowski, et al., "Efficient reduction of speckle noise in Optical Coherence Tomography," XP055044858, Optics Express, vol. 20, No. 2, 23 pgs. (Jan. 6, 2012).

* cited by examiner

X          L          S          N

REDUCING SPECKLE NOISE IN OPTICAL COHERENCE TOMOGRAPHY IMAGES

CROSS-REFERENCE TO RELATED APPLICATIONS

This patent application is a U.S. National Phase Application under 35 U.S.C. § 371 of International Application No. PCT/SG2015/050162, filed Jun. 16, 2015, entitled REDUCING SPECKLE NOISE IN OPTICAL COHERENCE TOMOGRAPHY IMAGES, which claims priority to Singapore Patent Application No. 10201403294R, filed Jun. 16, 2014.

FIELD OF THE INVENTION

Embodiments of the present invention relate to computer implemented methods and computer systems for processing optical coherence tomography image data to obtain reduced speckle noise images.

BACKGROUND OF THE INVENTION

Optical coherence tomography (OCT) is an optical signal acquisition and processing method. It captures micrometer-resolution, three-dimensional images from within optical scattering media (e.g., biological tissue). The principle of ocular imaging with OCT is based upon measuring the time-delay of the light reflected from each optical interface (A-scan) when a pencil of light enters the eye. A series of A-scans across the structure permits a cross-sectional reconstruction of a plane through the anterior or posterior segment of the eye. This is known as a B-scan.

Speckle noise is problematic for OCT imaging as well as other imaging modalities including synthetic aperture radar (SAR), remote sensing, ultrasound, sonar, etc. In these fields, a substantial amount of signal processing research has been conducted to combat speckle noise, resulting in the development of powerful digital filters for reducing speckle while preserving edge sharpness. Speckle reduction in OCT has been addressed by modifying imaging configurations and through the use of signal processing and image filtering. However, these methods often remove some details of the images and are unsuitable for OCT images in medical applications.

In typical OCT imaging, a single frame or slice of the image usually has very poor quality due to large speckle noise. Therefore, multiple scans are obtained and image averaging is applied, i.e., an average image is computed from the multiple image slices.

An example of an OCT system is the Topcon DRI OCT-1, a swept source OCT for posterior imaging, utilizing a wavelength of 1,050 nm. It has a scanning speed of 100,000 A-scans/sec. Utilizing this 1,050 nm wavelength, DRI OCT-1 can penetrate deeper compared to the current conventional OCTs with wavelength in the 850 nm range. Visualizing ocular tissues such as choroid or even sclera, can be done within a very short time. Deep range imaging DRI OCT-1 displays detail structures of not only retina but choroid and even sclera. With the capability of imaging deeper anatomic structures with less influence in scattering, DRI OCT-1 can visualize the entire tomogram with high sensitivity.

Depending on different applications and resolutions, different modes of scanning are provided in DRI OCT-1 including the line mode, 5 lines cross mode, 12 radial mode, circle line mode and 3D horizontal/vertical mode. In line mode, a line scan is conducted and repeated for a maximum of 96 times. In 5 line cross mode, 5 horizontal line scan and 5 vertical line scan are conducted with each line scan repeated for a maximum of 32 times. In 3D mode, a current swept source machine allows 4 repeated scans in 3D vertical mode with resolution 512×64 while each location is scanned only once in 3D horizontal model with 512×256 resolution. Since these scans are obtained from one location, they are averaged to get the final result with some help of image registration to overcome possible eye movement between different scans.

SUMMARY OF THE INVENTION

The present invention aims to provide a method of reducing speckle noise in optical coherence tomography (OCT) images. Matrix completion is used to reduce speckle noise. Matrix completion is the process of adding entries to a matrix which has some unknown or missing values. In general, given no assumptions about the nature of the entries, matrix completion is theoretically impossible, because the missing entries could be anything. However, given a few assumptions about the nature of the matrix, various algorithms allow it to be reconstructed. Matrix completion has been proven to be useful in noise reduction in other applications such as video and computed tomography imaging.

In order for matrix completion to be carried out, the input to the method is OCT image data which includes a plurality of cross sectional images of a subject. The cross sectional images each comprise a plurality of scan lines obtained by measuring the time delay of light reflected, in a depth direction, from optical interfaces within the subject.

The cross sectional images may be images of the same part of the subject, or they may be from neighbouring slices which can be used as the neighbouring slices have strong similarity.

The method comprises aligning the cross sectional images by determining relative translations for each cross sectional image in the depth direction and in a lateral direction, perpendicular to the depth direction, to form a set of aligned cross sectional images; aligning image patches of the aligned cross sectional images, each image patch comprising at least one scan line, by determining relative translations for each patch in the depth direction to form a set of aligned patches; forming an image matrix from the aligned patches; and applying matrix completion to the image matrix to obtain a reduced speckle noise image of the subject.

The application of matrix completion may involve decomposing the image matrix into a matrix representing a clean image part and a matrix representing a noise part.

Alternatively, applying matrix completion may involve decomposing the image matrix into a matrix representing a clean image part, a matrix representing a sparse part and a matrix representing a noise part.

In either of the methods discussed above the matrix representing the clean image part is a low rank matrix.

Before the cross sectional images are aligned, a preliminary de-noising process may be applied to reduce the speckle noise in the cross sectional images. The preliminary de-noising process may be, for example a speckle reduction anisotropic diffusion algorithm.

Following the method a filter such as an adaptive Weiner filter may be applied to the reduced speckle noise image of the subject.

A block matching algorithm may be applied to align the cross sectional images or to align image patches of the aligned cross sectional images. The block matching algorithm may be, for example the diamond search algorithm.

A smoothing process may be applied to the relative translations in the depth direction for each slice in the same cross sectional image to form the set of aligned patches.

As an embodiment of the invention, we propose a fast non-rigid two-step image registration algorithm for OCT images, where the first step is a global alignment and the second step is a local alignment. In addition, in the global and local alignments, we align the original raw OCT images based on their denoised version using a preliminary denosing process (speckle reduction anisotropic diffusion in our implementation).

Another technical feature is that we use bilateral random projections in low rank matrix completion to approximate the underlying clean images. Two models are used with the first model considering the OCT image as a sum of an underlying clean image part and a noise part, the second model considering the OCT image as a sum of an underlying clean image part, a sparse part due to movement and a noise part.

BRIEF DESCRIPTION OF THE DRAWINGS

In the following an embodiment of the present invention is described by way of example only with reference to the drawings, in which:

FIG. 3a illustrates a global registration and FIG. 3b illustrates a local registration;

FIG. 6a shows results obtained using the Image J noise model; and FIG. 6b shows results obtained using the Motion noise model.

DETAILED DESCRIPTION OF THE EMBODIMENT

Figure 1:
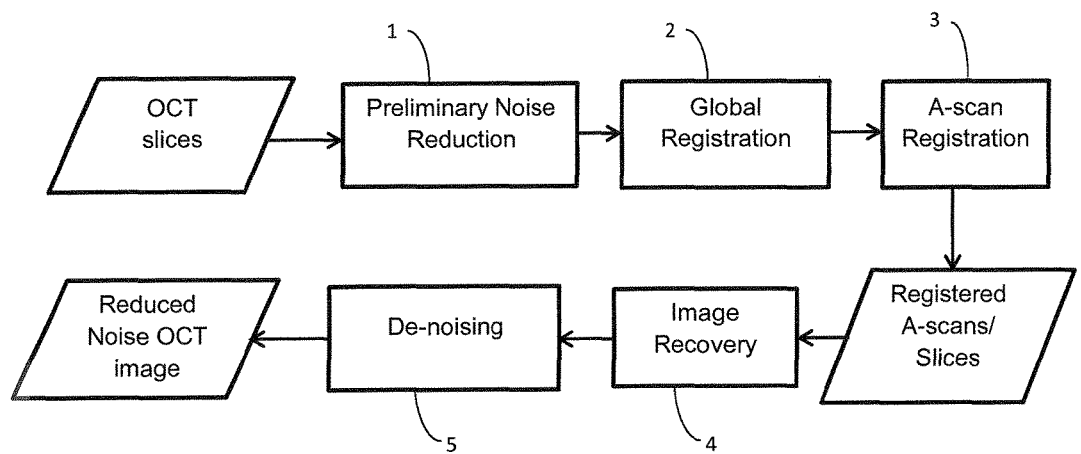
FIG. 1 is a flow chart illustrating a method of processing optical coherence tomography (OCT) data according to an embodiment of the present invention.

FIG. 1 is a flow chart illustrating a method of processing optical coherence tomography (OCT) data according to an embodiment of the present invention. The method may be performed by a computer system such as a standard generally programmed computer, having a data storage device storing program instructions to implement the method steps.

The input to the method is OCT data comprising a plurality of OCT slices. A requirement to use matrix completion is to obtain multiple slices for each scan. This is easy for line scan mode as each slice is scanned 96 times. For other modes such as 5 line-cross mode, 3D vertical and 3D horizontal mode, the scan from the neighbouring slice can be used as the neighbouring slices have strong similarity.

For example, in 5 lines cross mode, we use all the horizontal/vertical scans (5×32=160) for a horizontal/vertical slice. For 3D scans, we can use all 256 scans. Although many of these scans are obtained from different locations, many of the A-scans from the slices are similar. Therefore, we might make use of this similarity for noise reduction.

For simplicity, we assume that the input has K slices of OCT scans, including both the repeated scans from the same location and other scans from nearby locations. Each slice has p×q pixels.

In step 1 of the method, preliminary noise reduction is performed. Because of the inevitable movement when capturing the image slices, the original image slices may not match well. Therefore, it is necessary to align them to minimize the error. The original OCT slices are likely to be corrupted by large speckle noise.

Applying an image matching algorithm directly on these OCT slices may result in an unpredictable outcome due to the speckle noise. A pre-processing step is used to reduce the noise. Many algorithms can be used. In this embodiment we use the speckle reduction anisotropic diffusion algorithm.

The anisotropic diffusion algorithm is implemented as follows. Given an intensity image, the output image is evolved according to the partial differential equation (PDE):

$$\begin{cases} \frac{\partial I}{\partial t} = div[c(q) \cdot \nabla I] \\ I(t=0) = I_0 \end{cases},$$

where $c(q)$ denotes the diffusion coefficient computed with:

$$c(q) = 1/(1 + \lfloor q^2(x,y;t) - q_0^2(t) \rfloor / \lfloor q_0^2(t)(1 + q_0^2(t)) \rfloor) \text{ or}$$

$$c(q) = \exp\{-\lfloor q^2(x,y;t) - q_0^2(t) \rfloor / \lfloor q_0^2(t)(1 + q_0^2(t)) \rfloor\} \text{ and}$$

Figure 2:
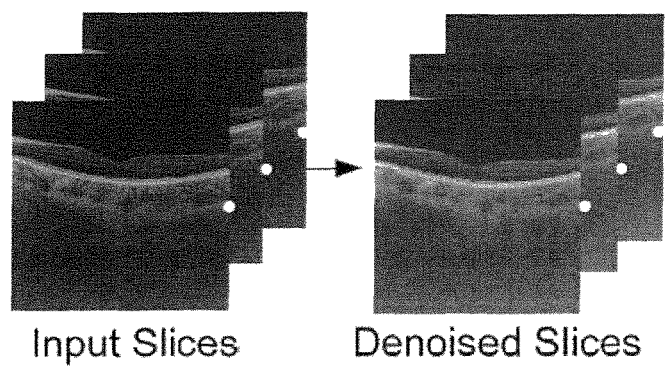
FIG. 2 shows an example of the preliminary de-noising process in an embodiment.

FIG. 2 shows an example of the preliminary de-noising process in an embodiment. Three input slices shown on the left hand side of FIG. 3 are processed using the speckle reduction anisotropic diffusion algorithm to provide the de-noised slices shown on the right hand side of FIG. 2.

Following the preliminary noise reduction, image registration between slices is carried out. The image registration between two slices (B-scans) is done by a global registration in step 2 followed by a local registration in step 3. Many methods can be used in the global registration.

Figure 3:
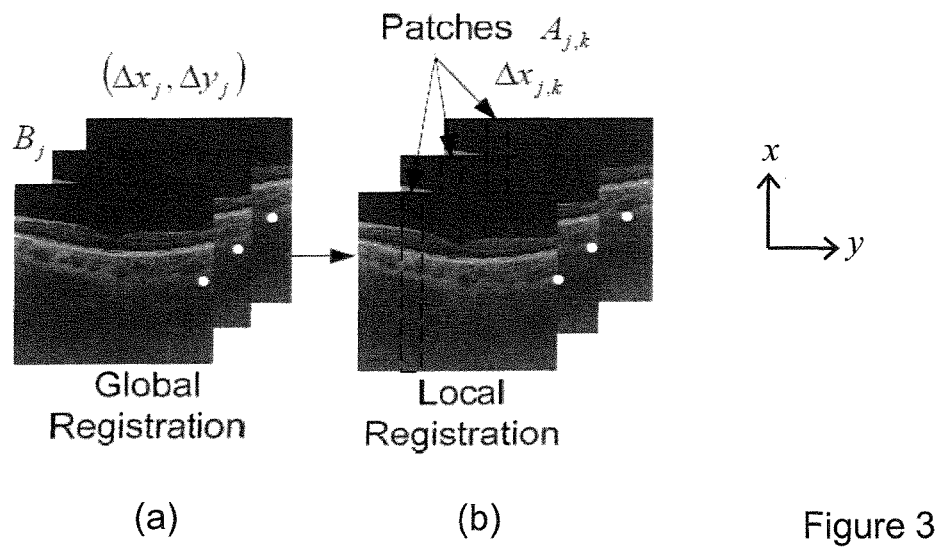
FIG. 3, which is composed of FIGS. 3a and 3b, illustrates the image registration steps.

FIG. 3 illustrates the image registration steps. FIG. 3a illustrates the global registration which is carried out in step 2 and FIG. 3b illustrates the local registration which is carried out in step 3.

In our implementation, the global registration is done by a global alignment, i.e., the entire slice (B-scan) is used in the matching by a translation in both horizontal (the y-direction) and vertical direction (the x-direction). The x-axis represents the direction in this the A-scans are carried out, that is a depth direction into the eye or subject being imaged. The y-axis represents a lateral direction, in which the A-scans are combined to form B-scans, perpendicular to the depth direction.

As shown in FIG. 3a, each slice $B_j$ is first translated by $(\Delta x_j, \Delta y_j)$ in the global registration. This is carried out according to the following process. Take an image $I_i$ as a reference, for each j, j=1, 2, ... K and j≠i find the translation $(\Delta x_j, \Delta y_j)$ between $I_i$ and $I_j$ such that their error is minimized. Therefore, we obtain a set of globally registered B-scan slices $B_i$, i=1, 2, ... K.

In the local registration, which is shown in FIG. 3b, an A-scan line or a group of neighbouring A-scan lines from one B-scan slice are translated vertically for best matching in the corresponding A-scans in the another B-scan slice.

This is carried out according to the following process. Divide $B_i$ to non-overlapping patches $A_{i,k}$, k=1, 2, ... P, where P is the number of patches obtained. Each patch has l columns or A-scan lines. For two corresponding patches $A_{i,k}$ and $A_{j,k}$ from two B-scans $B_i$ and $B_j$, find the vertical translation $\Delta x_{j,k}$ between them such that their error is minimized.

In order to avoid large error, patches/lines with poor matching can be discarded. Lines with poor matching may be identified and discarded by comparing the error with a threshold and discarding patches/lines with an error larger than the threshold. We apply vertical matching because each vertical line is an outcome of an A-scan and the movement within one A-scan is ignored.

Patient eye movements may be more obvious between different A-scans as time goes. Since the eye movement is expected to be smooth, a smoothing process is applied to the vertical translations $\Delta x_{j,k}$, k=1, 2, ... for lines in the same slice. It should be noted that the above patch is a line or an A-scan if we set l=1. Including multiple scan lines in the same patch helps to obtain a robust vertical translation. In another words, if we align one scan line with another line, the result may be more sensitive to the noise.

Many block matching algorithms can be used to find the alignment. In our implementation, we use the diamond search strategy for both global and local alignments because of its efficiency and easy implementation.

Once a set of aligned patches has been obtained in step 3, image recovery is carried out in step 4. After the image alignment, a set of aligned patches are obtained based on the global translation and the smoothed local translation. In order to recover an image, each aligned patch is vectorised to a row and stacked to form a matrix X with m rows. Each row in X has p·l elements from each vectorized patch. Each row of the matrix X has p·l elements and the matrix X has the number of B-slices of rows.

Once the image matrix, has been constructed, two possible methods of determining a reduced speckle noise image are possible.

Method 1: Decompose the X as a sum of low rank part and noise part, i.e., $$X = L + N, \quad (1)$$

Where L is the low rank part with rank (L)≤r, and N is the noise. In an implementation r is set to 2.

The above decomposition is solved by minimizing the decomposition error:

$$\min_L \|X - L\|_F^2, \text{ s.t. } \text{rank}(L) \leq r \quad (2)$$

The optimization problem above is solved by the bilateral random projections (BRP) algorithm.

The algorithm is summarized as follows:

---
Algorithm 1 for solving L
---
Generate a random matrix $A_1$
$A_1 \in R^{m \times r}$;
Compute $\tilde{L} = (XX^T)^q X$;
$Y_1 = \tilde{L} A_1, A_2 = Y_1$;
$Y_2 = \tilde{L}^T Y_1, Y_1 = \tilde{L} Y_2$
Calculate QR decomposition $Y_1 = Q_1 R_1$, $Y_2 = Q_2 R_2$;
$L = Q_1 [R_1 (A_2^T Y_1)^{-1} R_2^T]^{1/(2q+1)} Q_2^T$;

---

Method 2: In the second method, we decompose the X as a sum of low rank part, sparse part and noise part, i.e., $$X = L + S + N, \quad (1)$$

Where L is the low rank part with rank (L)≤r, S is the sparse part with card(S)≤k, k is a threshold which in one implementation is set as 30% of total elements in the matrix S, and N is the noise.

The above decomposition is solved by minimizing the decomposition error:

$$\min_{L,S} \|X - L - S\|_F^2, \text{ s.t. } \text{rank}(L) \leq r, \text{card}(S) \leq k. \quad (2)$$

The optimization problem above is solved by alternatively solving the following two sub-problems until convergence.

$$\begin{cases} L_t = \arg \min_{\text{rank}(L) \leq r} \|X - L_{t-1} - S_{t-1}\|_F^2 \\ S_t = \arg \min_{\text{card}(S) \leq k} \|X - L_{t-1} - S_{t-1}\|_F^2 \end{cases}$$

The algorithm is summarized as follows:

---
Algorithm 2 for solving L
---
Initialize t := 0; $L_0$ = X; $S_0$ = 0;
While $\|X - L_t - S_t\|_F^2 / \|X\|_F^2 > \varepsilon$, do
  t := t + 1;
  $\tilde{L} = [(X - S_{t-1})(X - S_{t-1})^T]^q (X - S_{t-1})$;
  Generate a random matrix $A_1 \in R^{m \times r}$;
  Compute $Y_1 = \tilde{L} A_1, A_2 = Y_1$;
  $Y_2 = \tilde{L}^T Y_1, Y_1 = \tilde{L} Y_2$
  Calculate QR decomposition $Y_1 = Q_1 R_1$, $Y_2 = Q_2 R_2$;
  If rank($A_2^T Y_1$) < r then r = rank($A_2^T Y_1$), go to the first step; end if;
  $L_t = Q_1 [R_1 (A_2^T Y_1)^{-1} R_2^T]^{1/(2q+1)} Q_2^T$;
  $S_t = \wp_\Omega(X - L_t)$, $\Omega$ is the nonzero subset of the first k largest entries of $|X - L_t|$; $\wp_\Omega$ is the projection of a matrix to $\Omega$.
End while

---

It can be see that the first method is a special case of the second method when S=0.

Once the speckle noise reduced image has been determined as described above, a post-process via filtering can be applied for de-noising in step 5. Step 5 may involve, for example, enhanced Lee, adaptive Wiener filters, etc. In this embodiment, an adaptive Wiener filter is used as an example. In addition, we also apply a threshold to assist the de-noising. Mathematically, we apply the following process:

$$L(x, y) = \begin{cases} T_{low} & L(x, y) < T_{low} \\ L(x, y) & T_{low} \leq L(x, y) \leq T_{high} \\ T_{high} & L(x, y) > T_{high} \end{cases}$$

Where $T_{low}$ and $T_{high}$ are two adaptively determined thresholds.

Figure 4:
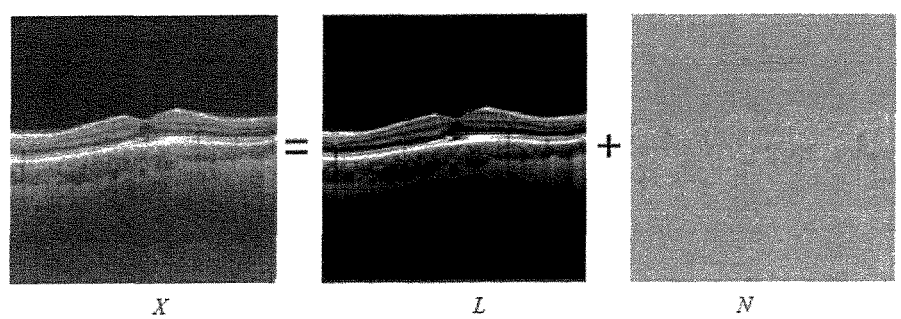
FIG. 4 shows an example of image recovery according a method in which an original image X is decomposed into the recovered image L and the noise N.

FIG. 4 shows an example of image recovery according to method 1 described above. The original image X is decomposed into the recovered image L and the noise N.

Figure 5:
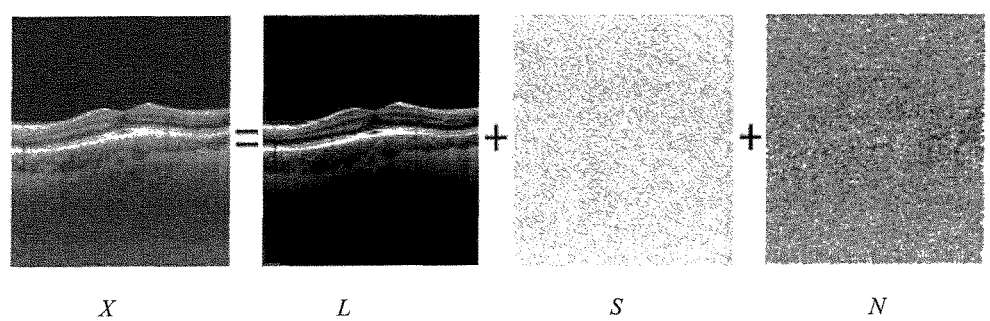
FIG. 5 shows an example of image recovery according a method in which an original image X is decomposed into the recovered image L a sparse part S and the noise N.

FIG. 5 shows an example of image recovery according to method 2 described above. The original image X is decomposed into the recovered image L a sparse part S and the noise N.

To evaluate the image quality, the contrast to noise ratio (CNR) is computed, which measures the contrast between image features and noise.

$$CNR = (1/R)\sum_1^R (\mu_r - \mu_b) / \sqrt{\sigma_r^2 + \sigma_b^2}$$

A total of 20 subjects are tested. Table 1 shows the results by a baseline approach and the two proposed methods using different noise models. In the first noise model we assume X=L+N and the second model refers to line 24 page 10 where we assume X=L+N+S. Although the second model gives higher CNR as shown in Table 1, we notice that the visual effect of the two models are similar.

TABLE 1

| | Objective measurement | |
|---|---|---|
| | Image Registration | |
| 96 slices | Image J | Motion |
| Baseline (Topcon) | 13.78 | 14.07 |
| X = L + N | 14.42 | 14.90 |
| X = L + S + N | 14.43 | 15.65 |

The baseline approach relies on the estimation of noise while the averaging relies on the cancel out among noise.

Figure 6:
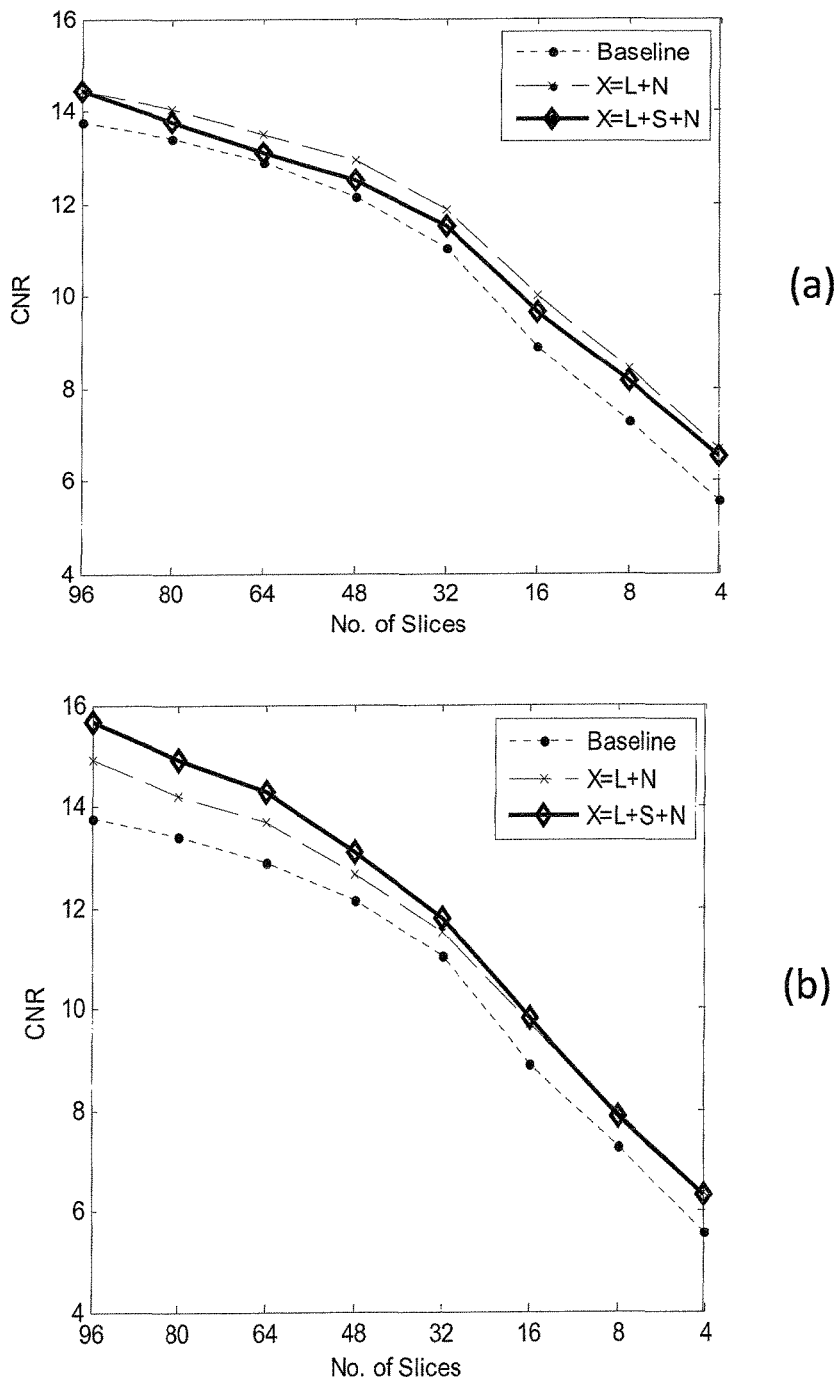
FIG. 6, which is composed of FIGS. 6a and 6b, shows a plot of the contrast to noise ratio (CNR) for the methods illustrated in FIGS. 4 and 5 with different numbers of slices.

FIG. 6 shows the plot of the CNR with different numbers of slices. FIG. 6a shows results obtained using the Image J noise model. FIG. 6b shows results obtained using the Motion noise model. As we can observe, the proposed methods using matrix completion outperform the baseline method.

In the embodiment described above, we solve the low rank recovery using bilateral random projection. It is faster than traditional algorithms such as robust principal component analysis (PCA). It takes about 5 s (algorithm 1) to 45 s (algorithm 2) to recover an image of 992×1024 pixels from 96 slice of 992×1024 pixels in a dual core 3.0 GHz PC with 3.25 GB RAM. Robust PCA requires 100 s for the same task for algorithm 1 and 15 mins for algorithm 2.

What is claimed is:

1. A computer implemented method of processing optical coherence tomography (OCT) image data, the OCT image data comprising a plurality of cross sectional images of a subject, each cross sectional image comprising a plurality of scan lines obtained by measuring the time delay of light reflected, in a depth direction, from optical interfaces within the subject, the method comprising:
aligning the cross sectional images by determining relative translations for each cross sectional image in the depth direction and in a lateral direction, perpendicular to the depth direction, to form a set of aligned cross sectional images;
dividing each aligned cross sectional image into a set of image patches across the lateral direction, each image patch comprising at least one scan line;
aligning the image patches of the aligned cross sectional images by determining relative translations for each image patch in the depth direction to form a set of aligned image patches;
forming an image matrix from the aligned image patches; and
applying matrix completion to the image matrix to obtain a reduced speckle noise image of the subject.

2. The method according to claim 1, wherein applying matrix completion to the image matrix comprises decomposing the image matrix into a matrix representing a clean image part and a matrix representing a noise part.

3. The method according to claim 2, wherein the matrix representing the clean image part is a low rank matrix.

4. The method according to claim 1, wherein applying matrix completion to the image matrix comprises decomposing the image matrix into a matrix representing a clean image part, a matrix representing a sparse part and a matrix representing a noise part.

5. The method according to claim 1, further comprising applying a preliminary de-noising process to the cross sectional images prior to aligning the cross sectional images.

6. The method according to claim 5, wherein the preliminary de-noising process is a speckle reduction anisotropic diffusion algorithm.

7. The method according to claim 1, further comprising applying a filter to the reduced speckle noise image of the subject.

8. The method according to claim 7, wherein the filter is an adaptive Weiner filter.

9. The method according to claim 1 wherein aligning the cross sectional images comprises applying a block matching algorithm.

10. The method according to claim 9, wherein the block matching algorithm is a diamond search algorithm.

11. The method according to claim 1 wherein aligning image patches of the aligned cross sectional images comprises applying a block matching algorithm between image patches of different cross sectional images.

12. The method according to claim 1, further comprising applying a smoothing process to the relative translations in the depth direction for each slice in the same cross sectional image to form the set of aligned patches.

13. The method according to claim 1, wherein the translations for the cross sectional images are determined relative to a common reference image.

14. The method according to claim 1, wherein for each aligned cross sectional image, the image patches divided therefrom are non-overlapping.

15. The method according to claim 1, wherein the cross sectional images are of different locations of the subject.

16. A computer system for processing optical coherence tomography (OCT) image data, the OCT image data comprising a plurality of cross sectional images of a subject, each cross sectional images comprising a plurality of scan lines obtained by measuring the time delay of light reflected, in a depth direction, from optical interfaces within the subject, the computer system having at least one processor and a data storage device storing program instructions, the program instructions being operative upon being run by the processor to cause the processor to:
align the cross sectional images by determining relative translations for each cross sectional image in the depth direction and in a lateral direction, perpendicular to the depth direction, to form a set of aligned cross sectional images;
divide each aligned cross sectional image into a set of image patches across the lateral direction, each image patch comprising at least one scan line;
align the image patches of the aligned cross sectional images by determining relative translations for each image patch in the depth direction to form a set of aligned image patches;

form an image matrix from the aligned image patches; and apply matrix completion to the image matrix to obtain a reduced speckle noise image of the subject.

* * * * *